US006876880B2

United States Patent
Hess et al.

(10) Patent No.: US 6,876,880 B2
(45) Date of Patent: Apr. 5, 2005

(54) AUTOMATED REAPPLICATION OF ATRIAL PACING THERAPIES

(75) Inventors: Michael F. Hess, Minneapolis, MN (US); Rahul Mehra, Stillwater, MN (US); Eduardo N. Warman, Maple Grove, MN (US); Nirav V. Sheth, Coon Rapids, MN (US); Mark L. Brown, North Oaks, MN (US); David Ritscher, Golden Valley, MN (US)

(73) Assignee: Medtronic, Inc., Minneapolis, MN (US)

( * ) Notice: Subject to any disclaimer, the term of this patent is extended or adjusted under 35 U.S.C. 154(b) by 456 days.

(21) Appl. No.: 10/034,060

(22) Filed: Dec. 20, 2001

(65) Prior Publication Data

US 2003/0120317 A1 Jun. 26, 2003

(51) Int. Cl.[7] ............................................... A61N 1/365
(52) U.S. Cl. ......................................................... 607/14
(58) Field of Search .............................. 607/5, 7, 9, 14, 607/15, 18, 27

(56) References Cited

U.S. PATENT DOCUMENTS

| | | |
|---|---|---|
| 4,467,810 A | * 8/1984 | Vollmann .................... 607/27 |
| 4,830,006 A | 5/1989 | Haluska et al. |
| 5,658,320 A | 8/1997 | Betzold et al. |
| 6,058,326 A | 5/2000 | Hess et al. |
| 6,078,837 A | 6/2000 | Peterson et al. .............. 607/14 |
| 6,272,380 B1 | 8/2001 | Warman et al. |

* cited by examiner

Primary Examiner—George Manuel
(74) Attorney, Agent, or Firm—Paul H. McDowall; Girma Wolde-Michael

(57) ABSTRACT

The invention relates to the use of atrial pacing therapies to treat atrial tachycardia (AT). When an AT episode is detected, an implantable medical device applies an ATP therapy. If the AT episode persists, the ATP therapy may be automatically reapplied at a later time during the course of the same AT episode. In particular, previously used ATP therapies are reapplied when episodic conditions, such as cycle length or cycle regularity, change. Although a particular ATP therapy initially may be unsuccessful in terminating the AT, it may prove successful when the cycle length or regularity of the atrial rhythm changes. As the rhythm slows down, the AT may be more responsive to ATP therapies that were previously unsuccessful. As a result, potentially efficacious ATP therapies can be reapplied to terminate AT episodes, and reduce the number of episodes that require more aggressive termination by painful, atrial shocks.

49 Claims, 7 Drawing Sheets

| RX(1) | RX(2) | RX(3) | RX(4) |
|---|---|---|---|
| ATP0 - DISARMED | ATP0 - DISARMED | ATP0 - DISARMED | ATP0 - ARMED |
| ATP1 - DISARMED | ATP1 - DISARMED | ATP1 - DISARMED | ATP1 - ARMED |
| ATP2 - DISARMED | ATP2 - DISARMED | ATP2 - DISARMED | ATP2 - ARMED |
| ATP3 - DISARMED | ATP3 - DISARMED | ATP3 - ARMED | ATP3 - ARMED |
| ATP4 - ARMED | ATP4 - DISARMED | ATP4 - ARMED | ATP4 - ARMED |
| ATP5 - ARMED | ATP5 - DISARMED | ATP5 - ARMED | ATP5 - ARMED |
| ATP6 - ARMED | ATP6 - DISARMED | ATP6 - ARMED | ATP6 - ARMED |
| ATP7 - ARMED | ATP7 - DISARMED | ATP7 - ARMED | ATP7 - ARMED |

AUTOMATED REAPPLICATION OF ATRIAL PACING THERAPIES

TECHNICAL FIELD

The invention relates to cardiac pacing systems and, more particularly, to systems for delivering atrial pacing therapies to treat atrial tachycardia.

BACKGROUND

An arrhythmia is a disturbance in the normal rate, rhythm or conduction of the heartbeat. An atrial arrhythmia originates in the atria. Atrial tachycardia (AT), one form of atrial arrhythmia, is a condition in which the atria contract at a high rate, e.g., 100 or more beats per minute. Atrial fibrillation (AF), another form of atrial arrhythmia, is characterized by a chaotic and turbulent activation of atrial wall tissue. The number of depolarizations per minute during AF can exceed 400. In addition, the AF stimuli can occur in the refractory period of the surrounding atrial myocardium.

AT can lead to AF, which in turn can be life threatening. Tachycardia is also associated with other low cardiac output symptoms, such as fatigue. Many atrial tachycardias are episodic, marked by abrupt onset but also abrupt termination, but cause considerable patient distress. If untreated, AT can lead to other dangerous life-threatening conditions, such as the development of blood clots which can cause stroke and possibly death.

Treatment for tachycardia may include anti-tachycardia pacing (ATP) or cardioversion, in which a train of high rate pulses or one or more high energy pulses is delivered to the heart in an attempt to restore a more normal rhythm. ATP is typically effective in converting stable atrial tachycardias to normal rhythm, and is often delivered via an implanted device. In many cases, a sequence of increasingly aggressive ATP therapies are applied until an episode of AT is terminated. The implanted device can be configured to discontinue ATP and immediately apply cardioversion in the event the AT degrades into atrial AF.

SUMMARY

In general, the invention is directed to the use of atrial pacing therapies to treat AT. The atrial pacing therapies can be applied by an implanted medical device. When an episode of AT is detected, the device applies an ATP therapy. If the episode persists, the ATP therapy may be automatically reapplied at a later time during the course of the AT episode. In particular, the invention involves reapplication of previously used ATP therapies when episodic conditions, such as cycle length or cycle regularity, change.

Although a particular ATP therapy initially may be unsuccessful in terminating the AT, it may prove successful when the cycle length or regularity of the atrial rhythm changes. For example, an atrial burst therapy may be ineffective for an AT at 140 beats per minute, but successfully return an AT at 110 beats per minute to a normal rhythm. Slowing of the AT may result from changes in vagal tone, medication, device therapy, reduced patient exertion, or other mechanisms.

As the rhythm slows down, the AT may be more responsive to ATP therapies that were previously unsuccessful in terminating the AT episode. The invention enables potentially efficacious ATP therapies to be reapplied as the AT rhythm changes even though they have already been applied for a different, e.g., faster, AT rhythm in the same episode.

In this manner, the invention is capable of increasing the efficacy of pacing techniques to terminate AT episodes and reduce the number of episodes that require more aggressive termination by painful, atrial shocks.

Reapplication of ATP therapies may be implemented, in some embodiments, by arranging a set of ATP therapy sequences. The sequences are assigned to a cycle length range and, optionally, a range of cycle regularity. Each sequence contains a number of ATP therapies that are applied consecutively until the AT is terminated, all of the ATP therapies in the sequence are exhausted, or the cycle length changes. The sequences are triggered when a characteristic of the heart rhythm, such as cycle length, falls into one of several detection "bins." Each detection bins contains one of the sequences of ATP therapies.

When the cycle length changes, and falls in a different detection bin, another sequence corresponding to the new cycle length is applied. The sequences may contain substantially identical ATP therapies. Accordingly, reapplication of an ATP therapy during an AT episode may occur when the same ATP therapies are applied from different sequences as cycle length changes. In some embodiments, different sequences may be established for both cycle length range and rhythm regularity. In either case, application of different sequences results in reapplication of given ATP therapies during the course of the AT episode.

In one embodiment, the invention provides a method comprising detecting an episode of atrial tachycardia in a human heart, applying an atrial pacing therapy to the heart to treat the atrial tachycardia, and automatically reapplying the atrial pacing therapy during the episode.

In another embodiment, the invention provides a system comprising a detector and a controller. The detector detects an episode of atrial tachycardia in a human heart. The controller applies an atrial pacing therapy to the heart to treat the atrial tachycardia, and automatically reapplies the atrial pacing therapy during the episode.

In an added embodiment, the invention provides a method comprising detecting an episode of atrial tachycardia in a human heart, and detecting a condition of the atrial tachycardia. The method further includes selecting one of several sequences of the atrial pacing therapies based on the detected condition, and applying the atrial pacing therapies in the selected sequence to treat the atrial tachycardia. Each of the applied atrial pacing in the selected sequence is disarmed to prevent reapplication of the applied atrial pacing therapies for the detected condition during the episode of atrial tachycardia. Following a predetermined period of time, the method rearms the applied atrial pacing therapies in the selected sequence to permit reapplication of the applied atrial pacing therapies for the detected condition during the episode of atrial tachycardia.

In a further embodiment, the invention provides a system comprising a detector that detects an episode of atrial tachycardia in a human heart and a condition of the atrial tachycardia, and a controller that selects one of several sequences of the atrial pacing therapies based on the detected condition and applies the atrial pacing therapies in the selected sequence to treat the atrial tachycardia. In addition, the controller disarms each of the applied atrial pacing in the selected sequence to prevent reapplication of the applied atrial pacing therapies for the detected condition during the episode of atrial tachycardia. Following a predetermined period of time, the controller rearms the applied atrial pacing therapies in the selected sequence to permit reapplication of the applied atrial pacing therapies for the detected condition during the episode of atrial tachycardia.

In another embodiment, the invention provides a computer-readable medium carrying instructions to cause a processor to detect an episode of atrial tachycardia in a human heart, apply an atrial pacing therapy to the heart to treat the atrial tachycardia, and automatically reapply the atrial pacing therapy during the episode.

In a further embodiment, the invention provides a computer-readable medium carrying instructions to cause a processor to: detect an episode of atrial tachycardia in a human heart, detect a condition of the atrial tachycardia, select one of several sequences of the atrial pacing therapies based on the detected condition, apply the atrial pacing therapies in the selected sequence to treat the atrial tachycardia, disarm each of the applied atrial pacing in the selected sequence to prevent reapplication of the applied atrial pacing therapies for the detected condition during the episode of atrial tachycardia, and, following a predetermined period of time, rearm the applied atrial pacing therapies in the selected sequence to permit reapplication of the applied atrial pacing therapies for the detected condition during the episode of atrial tachycardia.

The invention can provide a number of advantages. In general, the invention is capable of increasing the efficacy of termination of AT episodes by atrial pacing techniques, thereby reducing atrial tachyarrhythmia burden. In particular, the invention involves automated reapplication of ATP therapies when the AT episode presents a new rhythm that may be more susceptible to AT termination using previously applied ATP therapy. Instead of using an ATP therapy once during an AT episode and, in effect, discarding it, when the AT episode persists, the invention permits reuse of the ATP therapy at different rhythms. In this manner, the invention presents a greater likelihood that an ATP therapy will be successful at some point during the episode, reducing the necessity of painful shocks as the AT degrades into AF.

The details of one or more embodiments of the invention are set forth in the accompanying drawings and the description below. Other features, objects, and advantages of the invention will be apparent from the description and drawings, and from the claims.

BRIEF DESCRIPTION OF DRAWINGS

FIG. 6 is a diagram illustrating assignment of atrial pacing sequences to treat an episode of AT.

FIG. 8 is a diagram illustrating the arming status of ATP therapies within multiple atrial pacing sequences.

DETAILED DESCRIPTION

Figure 1:
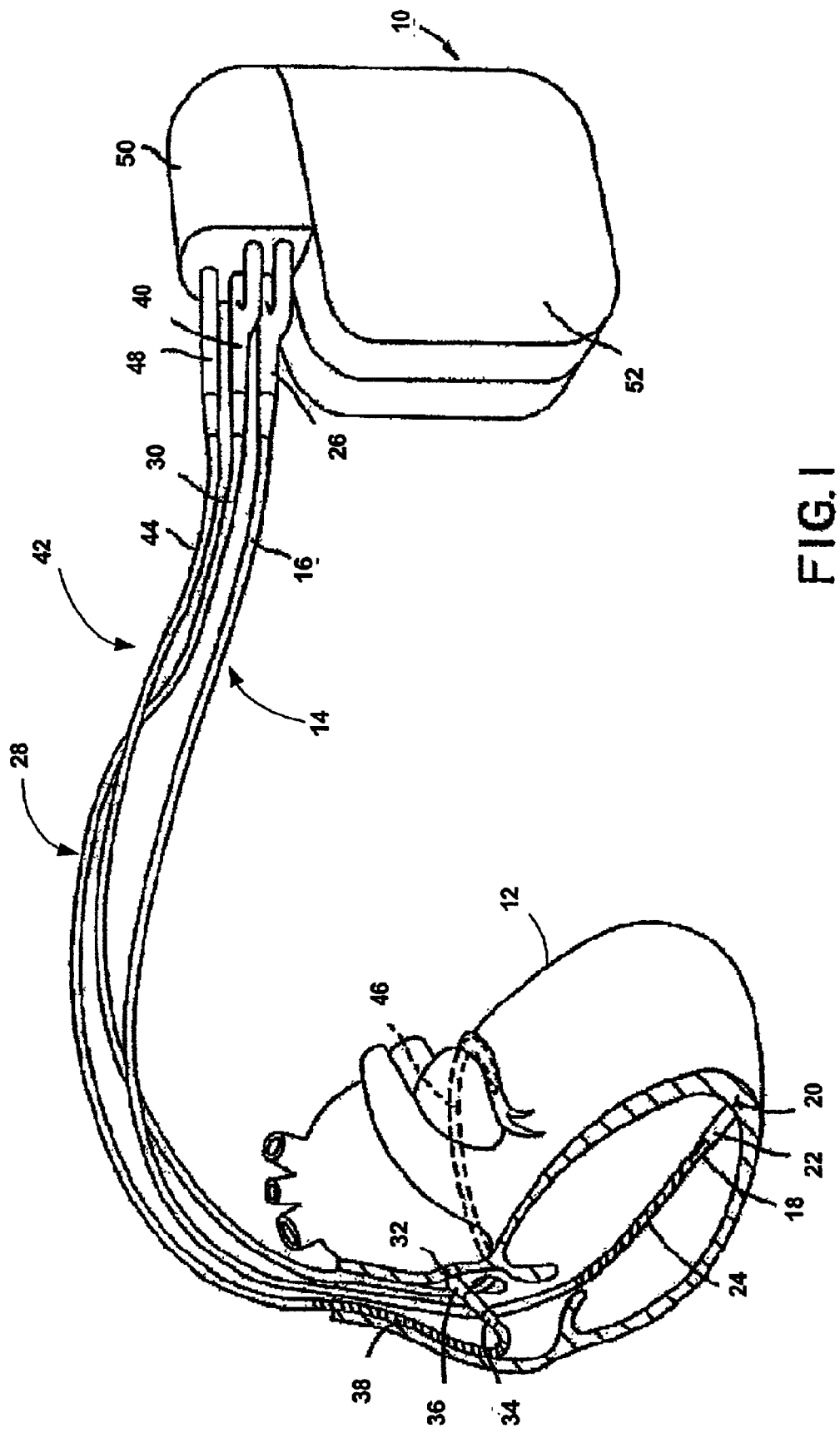
FIG. 1 is a diagram illustrating an implanted medical device useful in delivering anti-tachycardia pacing therapies.

FIG. 1 is a diagram illustrating an implanted medical device 10 useful in delivering anti-tachycardia pacing therapies. Device 10, shown in conjunction with a human heart 12, may be configured to deliver atrial pacing therapy as well as defibrillation shocks. As will be described, implanted medical device 10 can be configured to automatically reapply ATP therapies for different heart rhythms during an AT episode. The specific structure of device 10 is described below for purposes of example, and should not be considered limiting of the invention as broadly embodied herein.

As shown in FIG. 1, device 10 may include a ventricular lead 14 having an elongated insulative lead body 16, carrying three concentric coiled conductors, separated from one another by tabular insulative sheaths. Located adjacent the distal end of ventricular lead 14 are a ring electrode 18, an extendable helix electrode 20, mounted retractably within an insulative electrode head 22 and an elongated coil electrode 24. Each of electrodes 18, 20, 22, 24 is coupled to one of the coiled conductors within lead body 16. Electrodes 18, 20, 22, 24 can be used for both cardiac pacing and sensing of ventricular depolarizations. At the proximal end of ventricular lead 14 is a bifurcated connector 26 that carries three electrical connectors, each coupled to one of the coiled conductors.

An atrial/SVC lead 28 includes an elongated insulative lead body 30, carrying three concentric coiled conductors, separated from one another by tubular insulative sheaths. Located adjacent the J-shaped distal end of atrial lead 28 are a ring electrode 32 and an extendable helix electrode 34, mounted retractably within an insulative electrode head 36. Each of electrodes 32, 34, 36 is coupled to one of the coiled conductors within lead body 30. Electrodes 32, 34, 36 are employed for atrial pacing and for sensing atrial depolarizations. An elongated coil electrode 38 is provided proximal to ring electrode 32 and coupled to the third conductor within lead body 30. At the proximal end of lead 28 is a bifurcated connector 40 that carries three electrical connectors, each coupled to one of the coiled conductors.

A coronary sinus lead 42 includes an elongated insulative lead body 44, carrying one coiled conductor coupled to an elongated coiled defibrillation electrode 46. Electrode 46, illustrated in broken outline, is located within the coronary sinus and great vein of the heart. At the proximal end of lead 42 is a connector plug 48 that carries an electrical connector, coupled to the coiled conductor. Leads 14, 28, 42 are inserted into a connector block 51 associated with device 10. Device 10 has an outer housing 52 that may function as a subcutaneous defibrillation electrode that defibrillates either the atria or ventricles.

Figure 2:
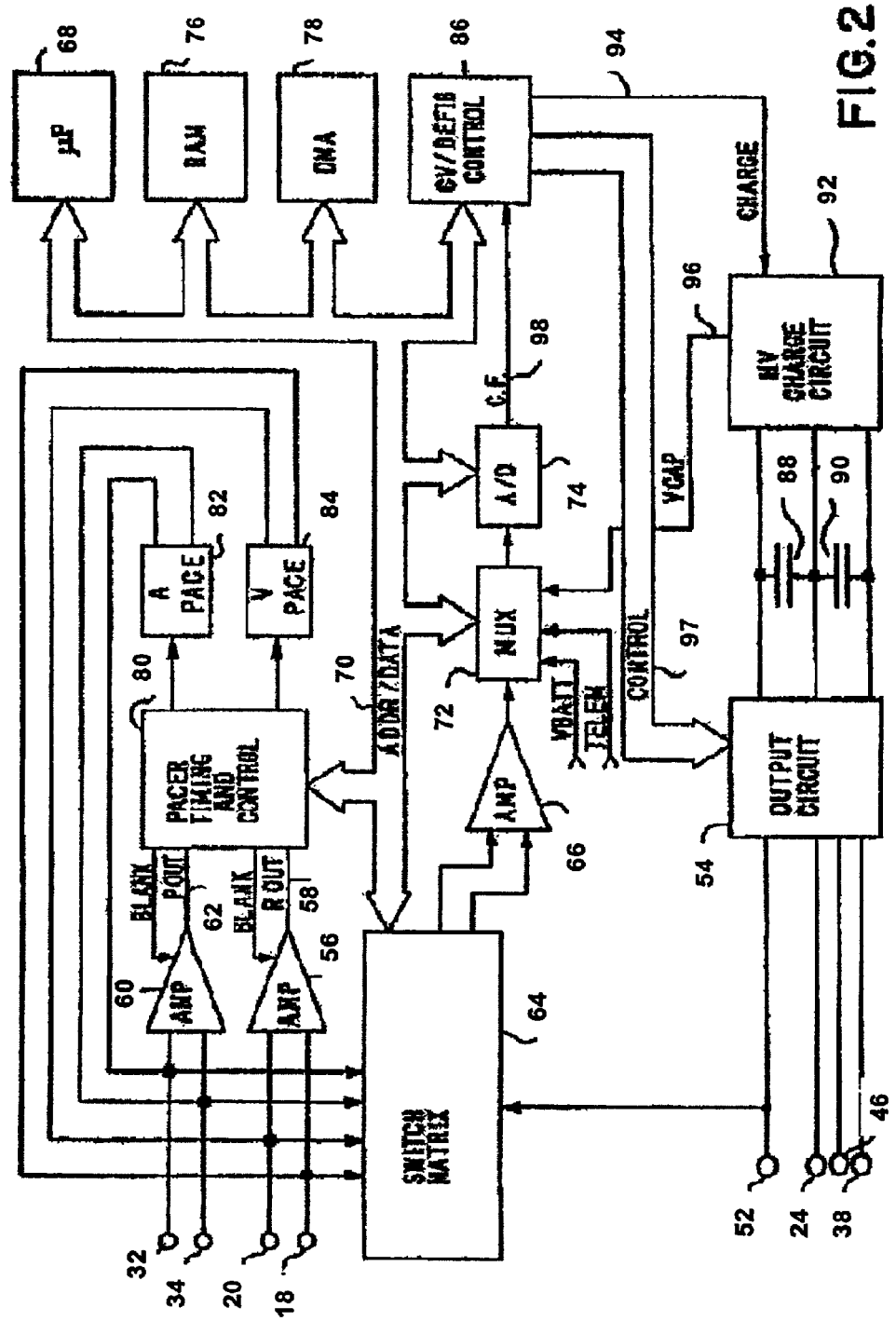
FIG. 2 is a functional schematic diagram illustrating a system capable of automated reapplication of atrial pacing therapies.

FIG. 2 is a functional schematic diagram illustrating a system capable of automated reapplication of atrial pacing therapies. The system may be implemented within device 10 of FIG. 1, and may take the form of an implantable device that integrates various pacemaker/cardioverter/defibrillator functions. The diagrams of FIGS. 1 and 2 should be taken as exemplary of the type of device in which the invention may be embodied, however, and as limiting of the invention as broadly embodied herein. For example, the invention may be practiced in a wide variety of device implementations, including devices providing therapies for treating atrial arrhythmias or both atrial and ventricular arrhythmias. In addition, the invention may be practice in antitachycardia pacemakers that do not provide cardioversion or defibrillation, as well as devices that deliver different forms of antiarrhythmia therapies such as nerve stimulation or drug administration.

In the example of FIG. 2, electrode 52 represents the uninsulated portion of the housing of device 10, which may function as a defibrillation electrode. Electrodes 24, 38, 46, 54 are coupled to high voltage output circuit 54. Electrodes 18, 20 are coupled to R-wave amplifier 56, which preferably takes the form of an automatic gain controlled amplifier providing an adjustable sensing threshold as a function of the measured R-wave amplitude. A signal is generated on R-out line 58 whenever the signal sensed between electrodes 18, 20 exceeds the present sensing threshold.

Electrodes 32, 34 are coupled to the P-wave amplifier 60, which also may take the form of an automatic gain controlled amplifier providing an adjustable sensing threshold as a function of the measured R-wave amplitude. A signal is generated on P-out line 62 when the signal sensed between electrodes 32, 34 exceeds the sensing threshold. Switch matrix 64 selects which of the available electrodes are coupled to wide band amplifier 66 for use in digital signal analysis. Selection of electrodes is controlled by a controller, which may take the form of a microprocessor 68. Microprocessor 68 controls selection of electrodes by switch matrix 64 via data/address bus 70. Signals from the electrodes selected for coupling to bandpass amplifier 66 are provided to multiplexer 72 and thereafter converted to multi-bit digital signals by A/D converter 74, for storage in random access memory (RAM) 76 under control of direct memory access circuit 78.

Microprocessor 68 may preferably employ digital signal analysis techniques to characterize the digitized signals stored in random access memory 76 to recognize and classify the heart rhythm using any of a variety of known signal processing methods. In particular, microprocessor 68 may implement a detector that monitors the cycle length and regularity of the heart rhythm during an AT episode. The remainder of the circuitry illustrated in FIG. 2 is dedicated to the provision of cardiac pacing, cardioversion and defibrillation therapies. Microprocessor 68 is programmed to control the circuitry of FIG. 2 to deliver ATP therapies in accordance with the invention. In addition, the circuitry of FIG. 2 functions in combination with microprocessor 68 to detect different heart rhythms for selection of ATP therapy sequences to be applied to heart 12.

Pacer timing/control circuitry 80 may include programmable digital counters that control the basic time intervals associated with DDD, VVI, DVI, VDD, AAI, DDI and other modes of single and dual chamber pacing well known to the art. More particularly, circuitry 80 is configured to control escape intervals associated with anti-tachyarrhythmia pacing in the atrium or both the atrium and ventricle. To treat an episode of tachyarrhythmia, circuitry 80 may employ known ATP therapies. In accordance with the invention, however, microprocessor 68 can be programmed to control circuitry 80 to reapply ATP therapies during an AT episode in response to detected changes in heart rhythm, as will be described.

Intervals defined by pacing circuitry 80 include atrial and ventricular pacing escape intervals, the refractory periods during which sensed P-waves and R-waves are ineffective to restart timing of the escape intervals and the pulse widths of the pacing pulses. The durations of these intervals are determined by microprocessor 68, in response to stored data in memory 76 and are communicated to the pacing circuitry 80 via address/data bus 70. Circuitry 80 also determines the amplitude of the cardiac pacing pulses under control of microprocessor 68.

During pacing, the escape interval counters within pacer timing/control circuitry 80 are reset upon sensing of R-waves and P-waves, and in accordance with the selected mode of pacing on time-out trigger generation of pacing pulses by pacer output circuits 82 and 84, which are coupled to electrodes 18, 20, 32, 34. The escape interval counters are also reset upon generation of pacing pulses, and thereby control the basic timing of cardiac pacing functions, including anti-tachyarrhythmia pacing.

The durations of the intervals defined by the escape interval timers are determined by microprocessor 68, via data/address bus 70. The value of the count present in the escape interval counters when reset by sensed R-waves and P-waves may be used to measure the durations of R-R intervals, P-P intervals, PR intervals and R-P intervals. The resulting measurements can be stored in memory 76 and used to detect tachyarrhythmias. To detect tachycardia and associated cycle length and regularity, the invention may employ any of a variety of known tachycardia detection algorithms.

In the event that an atrial tachyarrhythmia is detected, and an anti-tachyarrhythmia pacing regimen is desired, microprocessor 68 prescribes appropriate timing intervals for controlling generation of anti-tachyarrhythmia pacing therapies by pacer timing and control circuitry 80. In particular, the timing intervals control the operation of the escape interval counters in circuitry 80 and define refractory periods during which detection of R-waves and P-waves are ineffective to restart the escape interval counters.

In operation, microprocessor 68 selects one of several ATP therapy sequences based on characteristics of the heart rhythm, such as cycle length and regularity, as will be described. In the event that generation of a cardioversion or defibrillation pulse is required, microprocessor 68 employs the escape interval counter to control timing of cardioversion and defibrillation pulses, as well as associated refractory periods. In response to the detection of atrial or ventricular fibrillation or tachyarrhythmia requiring a cardioversion pulse, microprocessor 68 activates cardioversion/defibrillation control circuitry 86, which initiates charging of the high voltage capacitors 88, 90 via charging circuit 92, under control of high voltage charging control line 94. The voltage on high voltage capacitors 88, 90 is monitored via VCAP line 96, which is passed through multiplexer 72 and in response to reaching a predetermined value set by microprocessor 68, results in generation of a logic signal on Cap Full (CF) line 98, terminating charging. Thereafter, timing of the delivery of the defibrillation or cardioversion pulse is controlled by circuitry 86 via control bus 97. Following delivery of the fibrillation or tachycardia therapy, microprocessor 68 then returns device 10 to cardiac pacing and awaits the next pacing event or sensed atrial or ventricular depolarization.

Device 10 may be configured to apply an increasingly aggressive regimen of therapies. Upon initial detection of an AT, a sequence of atrial ATP therapies may be selected and delivered to the atrium. The sequence defines on order of ATP therapies to be applied in attempts to terminate the AT episode. The ATP therapies will typically be ordered from least to most aggressive. If the AT persists following application of the first ATP therapy, microprocessor 68 controls circuitry 80 to apply the next ATP therapy in the sequence. If the AT is not terminated, treatment continues using the other ATP therapies in the sequence.

Typically, if all of the ATP therapies in the sequence are applied without success, a higher level cardioversion pulse may be applied. The cardioversion pulse may be followed by cardioversion pulses with increased amplitudes in the event the AT episode still is not terminated. Cardioversion pulses cause significant pain and discomfort for the patient and are generally applied as a last resort. Accordingly, it is most desirable if the AT episode can be terminated prior to resorting to cardioversion. Moreover, application of defibrillation shocks is highly undesirable, but may be necessary if neither ATP therapies nor cardioversion are successful in converting the AT to a normal rhythm. A device and method in accordance with the invention are capable of increasing the success rates of ATP therapies. In this manner, the invention can be effective in avoiding cardioversion and defibrillation while reducing atrial tachyarrhythmia burden for the patient.

Figure 3:
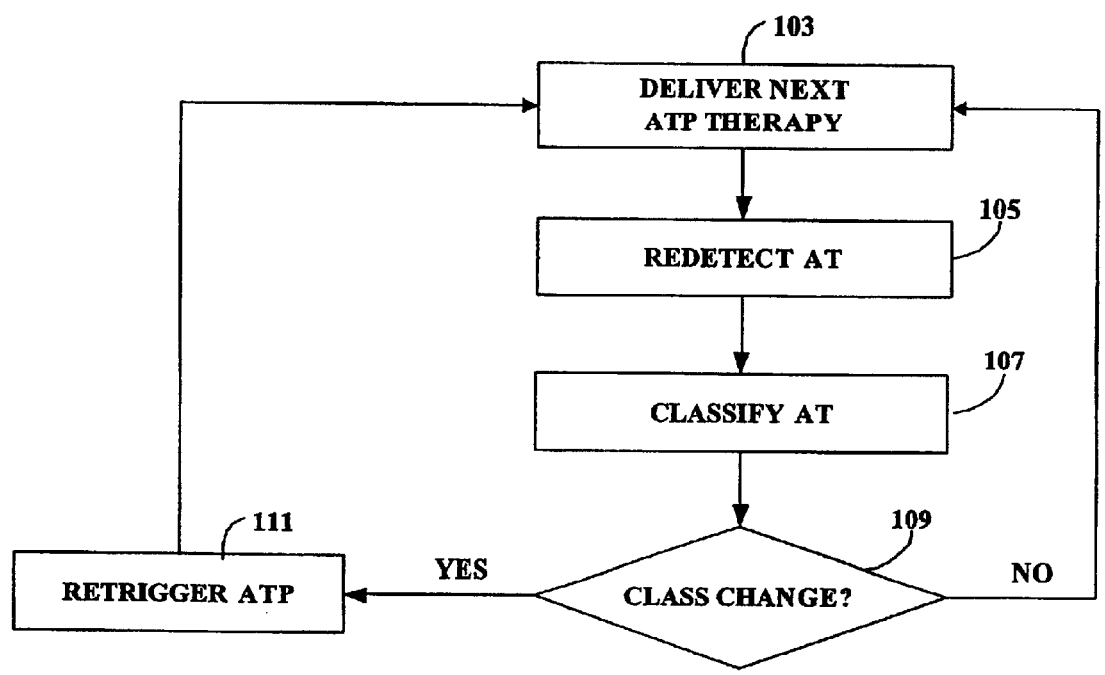
FIG. 3 is a flow diagram illustrating a method for automated reapplication of atrial pacing therapies.

FIG. 3 is a flow diagram illustrating a method for automated reapplication of atrial pacing therapies. The method may be implemented in device 10 as shown in FIGS. 1 and 2. As shown in FIG. 3, the method involves delivering the next ATP therapy available within a particular sequence of ATP therapies (103). Upon initial detection of the AT episode, the "next" ATP therapy may be the first ATP therapy available in the sequence. Otherwise, the next ATP therapy is the next therapy that has not yet been applied within the sequence.

The method further involves redetection of the AT (105). If the AT episode still persists following delivery of the ATP therapy, the AT is classified (107). The classification may be in terms of a cycle length associated with the heart rhythm. The classification also may be governed by one or more other conditions as alternatives or in addition to cycle length. For example, another condition may be regularity of the heart rhythm. As will be described, the heart rhythm may be divided into classes or zones characterized by a particular cycle length range and/or regularity.

Upon classification (107), the method determines whether the classification has changed since a previous classification (109). Initial detection of the AT episode is treated as a class change. If there is no change in the classification of the AT rhythm, the next unapplied ATP therapy in the sequence is applied (103). Following application, an ATP therapy within a given ATP sequence is "disarmed" so that it generally cannot be applied again. If there is a class change, however, the method "rearms" the ATP therapies (111) as will be explained. Following rearming (111), the next unapplied ATh therapy is delivered (103) to treat the AT.

In effect, the method of FIG. 3 permits a given ATP therapy to be applied more than once during the course of an AT episode. If the classification of the heart rhythm remains unchanged, an ATP therapy that has already been applied is "disarmed" and generally cannot be reapplied. Instead, only "armed" ATP therapies, i.e., those that have not been previously applied, can be delivered to treat the AT condition. If the classification changes, however, an ATP therapy that has been previously applied may be applied again. This feature of the invention recognizes that a particular ATP therapy may be more effective for a different rhythm.

Figure 4:
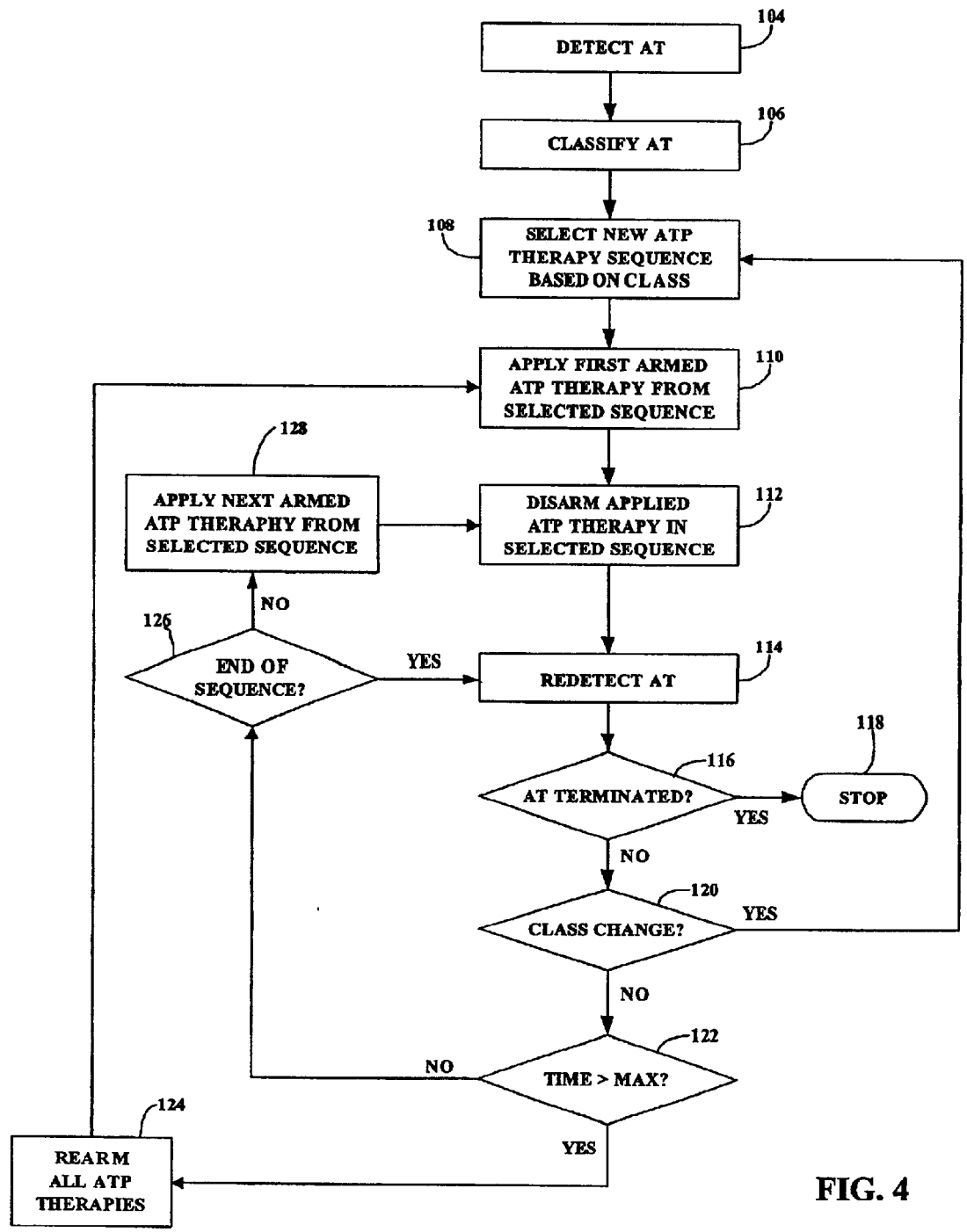
FIG. 4 is a flow diagram illustrating the method of FIG. 3 in greater detail.

FIG. 4 is a flow diagram illustrating the method of FIG. 3 in greater detail. As will be described with reference to FIG. 4, the "rearming" of the ATP therapies may be accomplished by designating several sequences of ATP therapies. Each sequence may contain a set of substantially identical ATP therapies, and be assigned to a particular classification of the heart rhythm. For example, the sequences may be assigned for application to AT heart rhythms with different ranges of cycle length. Once the ATP therapies in a first sequence are applied, they generally cannot be reapplied for the same heart rhythm. If the cycle length changes, however, a new sequence designated for the corresponding cycle length range is selected. By applying the ATP therapies in the new sequence, the method reapplies one or more of the same ATP therapies applied in the first sequence.

As shown in FIG. 4, when an AT is initially detected (104), the AT is classified (106), e.g., in terms of cycle length and/or regularity. The method selects a new ATP therapy sequence based on the resulting classification (108). The method then applies the first armed ATP therapy from the selected sequence (110). When a sequence is initially selected, all of the ATP therapies in the sequence are armed. If the sequence was already selected earlier, however, some or all of the ATP therapies may have been applied and are therefore disarmed. Upon application of the ATP therapy (110), the applied ATP therapy is disarmed. The ATP therapy is disarmed only for the selected sequence (112), however, and not for the other sequences that contain identical ATP therapies but apply to different rhythm classifications.

Upon disarming the ATP therapy (110), the AT is redetected (114). If the applied ATP therapy was successful in terminating the AT (116), the method ends (118). In this case, all of the ATP therapies are rearmed in preparation for the next AT episode, which may be hours, days or weeks away. If the AT is not terminated, however, the method determines whether the existing AT has changed its classification (120), e.g., based on cycle length or regularity. If so, the method selects a new ATP therapy sequence that corresponds to the pertinent class (108), and the process repeats itself.

If there is no classification change (120), the method determines whether the duration, i.e., time, of the AT episode has exceed a maximum time (122). This determination represents an optional mode of rearming in accordance with the invention. Specifically, ATP therapies can be rearmed by a classification change that drives selection of a different sequence of ATP therapies. Generally, when the ATP therapies within a sequence have been applied, they cannot be rearmed. In other words, applied ATP therapies within a particular sequence cannot be reapplied for the same heart rhythm.

Step 122 represents an optional time-based rearming, however, which permits rearming of all of the ATP therapies within a given sequence. The maximum time may be on the order of several hours. If an AT condition persists for an extended period of time, it may be worthwhile to attempt termination by reapplying ATP therapies that were tried several hours before. As an example, time-based rearming may be programmed by the physician with a default, e.g., of eight hours. Although it may be desirable to prescribe a maximum number of time-based rearmings of the ATP therapies, one or more time-based rearmings can be provided. Time-based rearming is designed to provide additional therapies for the long-duration tachyarrhythmias that have a large impact of patient burden.

If the time of the AT episode exceeds the maximum time, the method rearms all of the ATP therapies (128) and returns to step 110 to apply the first armed ATP therapy from the selected sequence, i.e., the sequence that applies to the current heart rhythm classification. If the time does not exceed the maximum time (122), the ATP therapies are not rearmed. Instead, the method determines whether the end of the selected sequence has been reached (126), i.e., whether all of the ATP therapies in the selected sequence have already been used. The end of the sequence is indicated when all of the ATP therapies in the sequence are disarmed. In some embodiments, time-based rearming may be programmed on or off by the physician.

Time-based rearming of all ATP therapies and reapplication of individual ATP therapies serve complementary purposes. Reapplication of individual ATP therapies is responsive to a change in rate or regularity and is particularly useful for arrhythmias that have short segments that regularize, or that only occasionally are pace terminable. Time-based rearming is periodic, based on elapsed time, and is particularly useful for arrhythmias that respond to ATP therapies most of the time, substrates where, due to sympathetic balance changes, arrhythmias become more responsive to ATP therapies despite no obvious change in rhythm, or rhythms that are constantly shifting.

If the end of the sequence has not been reached, the method applies the next armed ATP therapy from the selected sequence (128), disarms the applied ATP therapy (112) and commences AT detection again (114). If the end of the sequence has been reached, the method commences AT detection (114) and waits for a class change (120) or a time-based rearming (122, 124) before applying ATP therapy again. In each case, the method permits reapplication of an ATP therapy in an attempt to convert the AT to a normal rhythm. Indeed, in some cases, changes in vagal tone, medication, device therapy, reduced patient exertion, or other mechanisms may lead to rhythms that are more susceptible to conversion by an ATP therapy that has already been attempted.

In effect, at least part of one sequence of atrial pacing therapies are applied to the patient when the atrial rhythm represents AT with a cycle length in a first range. When the atrial rhythm represents AT with a cycle length in a second range, at least part of another sequence of atrial pacing therapies are applied. At least some of the atrial pacing therapies from the sequences are substantially identical. Accordingly, some of the therapies are automatically reapplied by applying substantially identical atrial pacing therapies from the first and second sequences when the cycle length of the atrial rhythm changes between the first range and the second range. Application of atrial pacing therapies from a given sequence generally continues until the episode of AT is terminated, the cycle length of the atrial rhythm is outside of the applicable range, or all of the atrial pacing therapies in the sequence have been applied.

Figure 5:
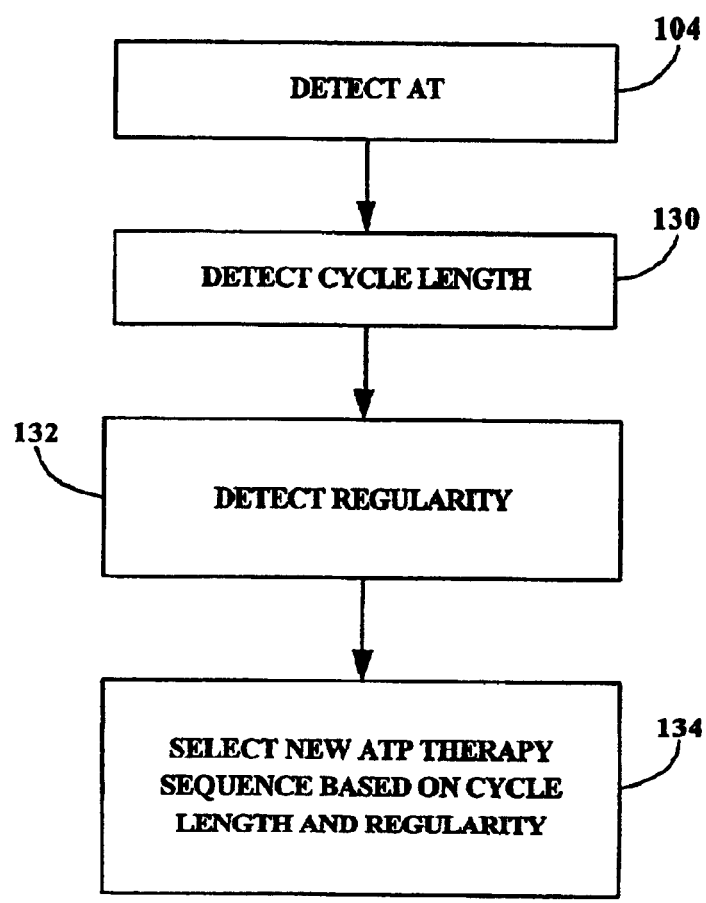
FIG. 5 is a diagram illustrating another aspect of the method of FIG. 4.

FIG. 5 is a diagram illustrating another aspect of the method of FIG. 4. In particular, FIG. 5 depicts one mode for classifying an AT condition. Upon AT detection (104), as in FIG. 4, the method detects the cycle length of the AT rhythm (130). In general, the cycle length is the interval between two consecutive heart beats, and indicates the rate of the AT rhythm. The cycle length determination (130) permits classification of faster and slower AT rhythms. The classification may also include detecting the regularity of the AT rhythm (132). The regularity of the AT rhythm generally refers to the periodicity of the rhythm and enables distinction of regular rhythms from rhythms indicating the possible onset of AF. Based on the classification, the method selects a new ATP therapy sequence (134). In particular, the method selects a sequence that has been designated for the applicable range of cycle length and regularity.

Figure 6:
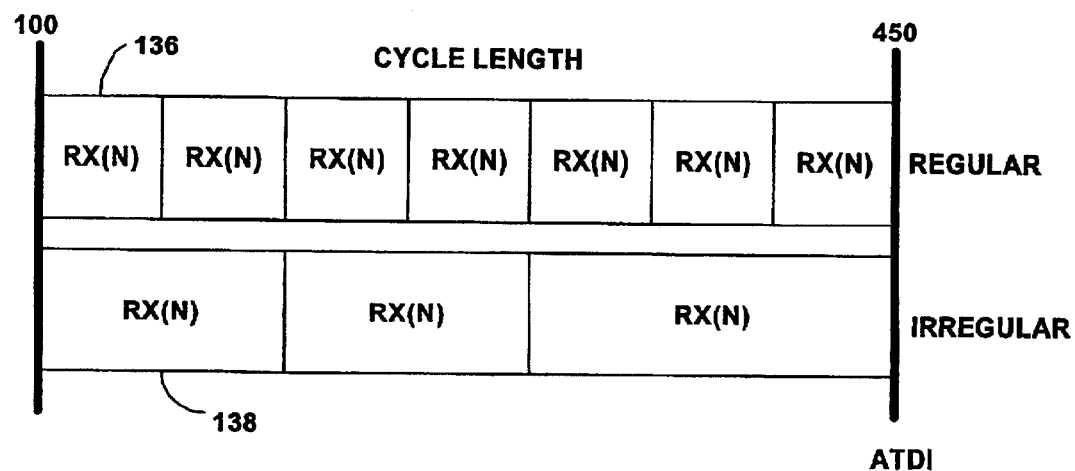

FIG. 6 is a diagram illustrating assignment of atrial pacing sequences to treat an episode of AT. In accordance with the invention, an AT episode can be divided into one or more zones. The example of FIG. 6 illustrates the use of a single zone for an AT episode. The zone has two bands, one for regular rhythms and one for irregular rhythms. In the example of FIG. 6, the regular rhythm band is divided into seven different detection bins. Each bin contains a sequence RX(N) of ATP therapies for regular rhythms with cycle lengths between 100 and 450 milliseconds (ms). The seven different bins are indicated by reference numeral 136.

For irregular rhythms with cycle lengths between 100 and 450 ms, there are three additional bins representing ATP therapy sequences RX(N), indicated by reference numeral 138. Thus, the complete zone is divided into seven bins for regular rhythms and three bins for irregular rhythms, resulting in ten preset detection bins. The 450 ms value in this example represents the atrial tachyarrhythmia detection interval (ATDI), which may be programmed into microprocessor 68 by a physician. The 100 ms value may represent the fast ATDI (FATDI) that serves as a boundary between a fast arrhythmia and a slower arrhythmia.

Each bin 136, 138 has a sequence of N pacing therapies arranged in order of application to treat an AT condition. The N pacing therapies in bins 136 for regular rhythms may be equal in number and substantially identical to another. For example, each bin 136 may include a sequence of one or more atrial burst therapies, one or more atrial ramp therapies, and one or more atrial cardioversion therapies, e.g., at different amplitude levels. Each bin 136 preferably is arranged from least aggressive to most aggressive ATP therapy. Each bin 138 may be similarly arranged, but may start at a more aggressive ATP therapy and generally include more aggressive ATP therapies in light of the irregularity of the heart rhythm. Thus, in some embodiments, bins 136 may be substantially identical, whereas bins 138 may differ significantly from sequences 138. In particular, each sequence may contain a set of pacing therapies selected by a physician. Notably, bins 136 need not be identical to one another.

Each bin 136 corresponds to a particular cycle length range for a regular rhythm. For purposes of example, a first bin may correspond to a cycle length of 100 to 150 ms, whereas a second bin may correspond to a cycle length of 150 to 200 ms. Similarly, each bin 138 corresponds to a cycle length range for an irregular rhythm. Bins 138 may cover cycle length ranges of roughly 100 to 200 ms, 200 to 300 ms, and 300 to 450 ms. When an AT rhythm is classified as having a particular cycle length range and regularity, the corresponding bin 136, 138 is selected for application to treat the AT condition. As ATP therapies in a bin are applied, they are disarmed. However, an ATP therapy may be reapplied during the same AT episode when cycle length changes, and a different bin having a sequence of identical ATP therapies is selected.

As an illustration, when an AT is initially detected, it is classified into one of the ten detection bins shown in FIG. 6, and the first therapy of the sequence contained in that bin is applied. If AT is redetected, the rhythm is again classified into one of the bins. If the classification points to the same bin, the second therapy of that bin is applied. Otherwise, the first therapy in a new bin is applied. The process continues so that with each redetection, the appropriate bin is selected and the next armed therapy in that bin is delivered. When all N therapies in a bin have been delivered, the device will not deliver further therapy until redetection points to a new bin with at least one armed therapy or a time-based rearming has resulting in rearming of all the bins.

Figure 7:
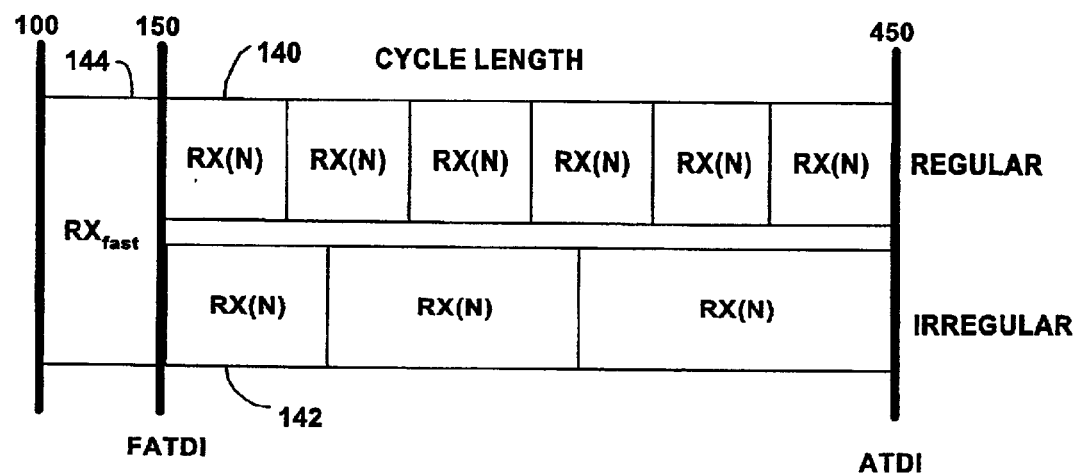
FIG. 7 is a diagram illustrating assignment of atrial pacing sequences to distinguish between moderate tachycardia and fast tachycardia within an episode of tachycardia.

FIG. 7 is a diagram illustrating assignment of atrial pacing sequences to distinguish between moderate tachycardia and fast tachycardia within an episode of tachycardia. The diagram of FIG. 7 conforms substantially to that shown in FIG. 6. However, the diagram of FIG. 7 illustrates assignment of two zones. Specifically, AT detection is divided into a first zone with two bands (regular and irregular) as in FIG. 6, but also includes a second zone for fast arrhythmias.

In the example of FIG. 7, the first zone may assign bins 140, 142 that extend between 150 and 450 ms. However, an additional zone assigns a detection bin 144 to both regular and irregular rhythms from 100 to 150 ms. Detection bin 144 may contain a sequence of ATP therapies that are more aggressive than those prescribed by bins 140, 142 in order to more aggressively treat faster arrhythmias.

The zones in FIG. 7 are characterized as an FATDI boundary, which may be specified by the physician. When programmed as a two-zone system, there are two separate sets of pacing therapies that can be provided. In some cases, a physician may elect to load bin 144 in the fast arrhythmia zone with no pacing therapies or a different set of therapies appropriate for very fast rhythms.

In the case of time-base rearming, all ATP therapies in both zones may be rearmed. Combining time-based rearming and reapplication of ATP therapies can help assure availability of atrial pacing therapies over an extended time window. The physician can customize the therapy based on patient difference by adjusting whether both time-based rearming and reapplication of ATP therapies are turned on, and by adjusting the time and conditions for rearming and reapplication, respectively.

For example, a patient with a very regular rhythm might deplete, i.e., apply and disarm, ATP therapies in only one or two detection bins. As a result, there would be ATP therapies available for a later shift in rhythm. In this example, time-based rearming may be less important. Conversely, in a patient with a wide range of rhythms, a number of detection bins could be depleted. In this case, setting the rearming time to a shorter interval may be advisable to ensure that additional therapies are available at a later time.

FIG. 8 is a diagram illustrating the arming status of ATP therapies within multiple sequences. In the example of FIG. 8, four adjacent detection bins 150, 152, 154, 156 are designated for cycle lengths of 150 to 200 ms, 200 to 250 ms, 250 to 300 ms, and 300 to 350 ms. Each bin contains a sequence of ATP therapies ATP0–ATP7. As the AT rhythm is classified into one of the detection bins, i.e., in terms cycle length, the therapies from that bin are applied to treat the AT episode. The therapies are applied in sequence until (a) the classification changes, in which case therapies in another bin are applied, (b) all of the therapies in the bin have been applied and are disarmed (subject to time-based rearming), or (c) the AT episode is terminated.

As shown in FIG. 8, the sequence of the first bin 150 has been applied up to ATP3. In the case of bin 152, all of the therapies ATP0–ATP7 have been applied and are disarmed. As in bin 150, some of the therapies in bin 154 have been applied. However, bin 156 contains a full sequence of armed ATP therapies. If the AT episode were classified into bin 156, treatment would start with application of ATP therapy ATP0. In contrast, if the AT episode were classified into bin 154, treatment would start with application of ATP therapy ATP3. Finally, if the AT episode were classified into bin 152, no therapy would be applied because all of the therapies in that bin have been previously applied and are disarmed.

Various embodiments of the invention have been described. These and other embodiments are within the scope of the following claims.

What is claimed is:

1. A method comprising:

detecting an episode of atrial tachycardia in a heart;

applying an atrial pacing therapy to the heart in an attempt to terminate the atrial tachycardia; and automatically reapplying the atrial pacing therapy during the non-terminated episode and further comprising:

applying at least part of a first sequence of atrial pacing therapies when the atrial rhythm represents atrial tachycardia with a cycle length in a first range; and applying at least part of a second sequence or atrial pacing therapies when the atrial rhythm represents atrial tachycardia with a cycle length in a second range, wherein at least some of the atrial pacing therapies from the first and second sequences are substantially identical; and automatically reapplying the atrial pacing therapy by applying at least one of the substantially identical atrial pacing therapies from the first and second sequences when the cycle length of the atrial rhythm changes between the first range and the second range.

2. The method of claim 1, further comprising reapplying the atrial pacing therapy in response to a change in atrial tachycardia rhythm.

3. The method of claim 2, further comprising reapplying the atrial pacing therapy in response to a change in a cycle length of the atrial tachycardia rhythm.

4. The method of claim 2, further comprising reapplying the atrial pacing therapy in response to a change in regularity of the atrial tachycardia rhythm.

5. The method of claim 1, further comprising reapplying the atrial pacing therapy following elapse of a predetermined period at time.

6. The method of claim 1, further comprising:

applying a plurality of different atrial pacing therapies; and automatically reapplying at least one of the plurality of different atrial pacing therapies during the non-terminated episode.

7. The method of claim 1, further comprising:

applying each of the atrial pacing therapies in the first sequence until the episode of atrial tachycardia is terminated, the cycle length of the atrial rhythm is outside of the first range, or all of the atrial pacing therapies in the first sequence have been applied; and in the event the cycle length of the atrial rhythm reenters the first range, applying any unapplied atrial pacing therapies in the first sequence until the episode of atrial tachycardia is terminated, the cycle length of the atrial rhythm is outside of the first range, or all of the atrial pacing therapies in the first sequence have been applied.

8. The method of claim 7, further comprising:

disarming each of the applied atrial pacing therapies in the first sequence to prevent reapplication of the applied atrial pacing therapies in the first sequence during the episode of atrial tachycardia; and following a predetermined period of time, rearming the applied atrial pacing therapies in the first sequence to permit reapplication of the applied atrial pacing therapies in the first sequence during the episode of atrial tachycardia.

9. The method of claim 8, further comprising:

applying each of the atrial pacing therapies in the second sequence until the episode of atrial tachycardia is terminated, the cycle length of the atrial rhythm is outside of the second range, or all of the atrial pacing therapies in the second sequence have been applied; and in the event the cycle length of the atrial rhythm reenters the second range, applying any unapplied atrial pacing therapies in the second sequence until the episode of atrial tachycardia is terminated, the cycle length of the atrial rhythm is outside of the second range, or all of the atrial pacing therapies in the second sequence have been applied.

10. The method of claim 9, further comprising:

disarming each of the applied atrial pacing therapies in the second sequence to prevent reapplication of the applied atrial pacing therapies in the first sequence during the episode of atrial tachycardia; and following a predetermined period of time, rearming the applied atrial pacing therapies in the first sequence to permit reapplication of the applied atrial pacing therapies in the first sequence during the episode of atrial tachycardia.

11. The method of claim 1, wherein the atrial pacing therapies in each of the first and second sequences are arranged in sequential order from least aggressive to most aggressive.

12. The method of claim 1, wherein the atrial pacing therapies in each of the first and second sequences include an atrial burst therapy, an atrial ramp therapy, and atrial cardioversion.

13. The method of claim 1, further comprising:

applying one of a defibrillation and a cardioversion therapy to the heart in the event an irregular heart rhythm satisfies predetermined criteria for application of the defibrillation or cardioversion therapy; and just prior to applying the defibrillation or cardioversion therapy, reapplying a sequence of the atrial pacing therapies to attempt to terminate the episode of atrial tachycardia.

14. The method of claim 1, further comprising applying the atrial pacing therapy via an implanted medical electrical lead.

15. A method comprising:

detecting an episode of atrial tachycardia in a heart;

applying an atrial pacing therapy to the heart in an attempt to terminate the atrial tachycardia; and automatically reapplying the atrial pacing thereby during the non-terminated episode and further comprising:

applying at least part of a first sequence of atrial pacing therapies when the atrial rhythm has a cycle length in a first range and the cycle length is substantially regular;

applying at least part of a second sequence of atrial pacing therapies when the atrial rhythm has a cycle length in a second range and the cycle length is substantially regular;

applying at least part of a third sequence of atrial pacing therapies when the atrial rhythm is irregular, wherein at least some of the atrial pacing therapies from the first, second and third sequences are substantially identical; and automatically reapplying the atrial pacing therapy by applying at least some of the substantially identical atrial pacing therapies from the first, second and third sequences.

16. The method of claim 15, further comprising:

applying each of the atrial pacing therapies in the third sequence until the episode of atrial tachycardia is terminated, the cycle length of the atrial rhythm is regular, or all of the atrial pacing therapies in the third sequence have been applied in the event the cycle length of the atrial rhythm becomes irregular, applying any unapplied atrial pacing therapies in the third sequence until the episode of atrial tachycardia is terminated, the cycle length of the atrial rhythm is regular, or all of the atrial pacing therapies in the third sequence have been applied.

17. The method of claim 16, further comprising:

disarming each of the applied atrial pacing therapies in the third sequence to prevent reapplication of the applied atrial pacing therapies in the third sequence during the episode of atrial tachycardia; and following a predetermined period of time, rearming the applied atrial pacing therapies in the third sequence to permit reapplication of the applied atrial pacing therapies in the third sequence during the episode of atrial tachycardia.

18. The method of claim 17, wherein the atrial pacing therapies in the third sequence are arranged in sequential order from least aggressive to most aggressive.

19. The method of claim 18, wherein the atrial pacing therapies in the third sequence include an atrial burst therapy, atrial ramp therapy, arid atrial cardioversion.

20. A system comprising:

a detector that detects an episode of atrial tachycardia in a heart; and a controller that applies an atrial pacing therapy to the heart in an attempt to terminate the atrial tachycardia episode, and automatically reapplies the atrial pacing therapy during the non-terminated episode, wherein the controller:

applies at least part of a first sequence of atrial pacing therapies when the atrial rhythm represents atrial tachycardia with a cycle length in a first range; and applies at least part of a second sequence of atrial pacing therapies when the atrial rhythm represents atrial tachycardia with a cycle length in a second range, wherein at least some of the atrial pacing therapies from the first and second sequences are substantially identical; and automatically reapplies the atrial pacing therapy by applying at least one of the substantially identical atrial pacing therapies from the first and second sequences when the cycle length of the atrial rhythm changes between the first range and the second range.

21. The system of claim 20, wherein the controller reapplies the atrial pacing therapy in response to a change in atrial rhythm.

22. The system of claim 21, wherein the controller reapplies the atrial pacing therapy in response to a change in a cycle length of the atrial rhythm.

23. The system of claim 21, wherein the controller reapplies the atrial pacing therapy in response to a change in regularity of the atrial rhythm.

24. The system of claim 20, wherein the controller reapplies the atrial pacing therapy following elapse of a predetermined period of time.

25. The system of claim 20, wherein the controller applies a plurality of atrial pacing therapies, and automatically reapplies at least one of the atrial pacing therapies during the episode.

26. The system of claim 20, wherein the controller:

applies each of the atrial pacing therapies in the first sequence until the episode of atrial tachycardia is terminated, the cycle length of the atrial rhythm is outside of the first range, or all of the atrial pacing therapies in the first sequence have been applied; and in the event the cycle length of the atrial rhythm reenters the first range, applies any unapplied atrial pacing therapies in the first sequence until the episode of atrial tachycardia is terminated, the cycle length of the atrial rhythm is outside of the first range, or all of the atrial pacing therapies in the first sequence have been applied.

27. The system of claim 26, wherein the controller:
disarms each of the applied atrial pacing therapies in the first sequence to prevent reapplication of the applied atrial pacing therapies in the first sequence during the episode of atrial tachycardia; and
following a predetermined period of time, rearms the applied atrial pacing therapies in the first sequence to permit reapplication of the applied atrial pacing therapies in the first sequence during the episode of atrial tachycardia.

28. The system of claim 27, wherein the controller:
applies each of the atrial pacing therapies in the second sequence until the episode of atrial tachycardia is terminated, the cycle length of the atrial rhythm is outside of the second range, or all of the atrial pacing therapies in the second sequence have been applied; and
in the event the cycle length of the atrial rhythm reenters the second range, applies any unapplied atrial pacing therapies in the second sequence until the episode of atrial tachycardia is terminated, the cycle length of the atrial rhythm is outside of the second range, or all of the atrial pacing therapies in the second sequence have been applied.

29. The system of claim 28, wherein the controller:
disarms each of the applied atrial pacing therapies in the second sequence to prevent reapplication of the applied atrial pacing therapies in the first sequence during the episode of atrial tachycardia; and
following a predetermined period of time, rearms the applied atrial pacing therapies in the first sequence to permit reapplication of the applied atrial pacing therapies in the first sequence during the episode of atrial tachycardia.

30. The system of claim 20, wherein the atrial pacing therapies in each of the first end second sequences are arranged in sequential order from least aggressive to most aggressive.

31. The system of claim 20, wherein the atrial pacing therapies in each of the first and second sequences include an atrial burst therapy, an atrial ramp therapy, and atrial cardioversion.

32. The system of claim 20, wherein the controller:
applies at least part of a first sequence of atrial pacing therapies when the atrial rhythm has a cycle length in a first range and the cycle length is substantially regular;
applies at least part of a second sequence of atrial pacing therapies when the atrial rhythm has a cycle length in a second range and the cycle length is substantially regular;
applies at least part of a third sequence of atrial pacing therapies when the atrial rhythm is irregular, wherein at least some of the atrial pacing therapies from the first, second and third sequences are substantially identical; and
automatically reapplies the atrial pacing therapy by applying at least some of the substantially identical atrial pacing therapies from the first, second and third sequences.

33. The system of claim 32, wherein the controller:
applies each of the atrial pacing therapies in the third sequence until the episode of atrial tachycardia is terminated, the cycle length of the atrial rhythm is regular, or all of the atrial pacing therapies in the third sequence have been applied in the event the cycle length of the atrial rhythm becomes irregular, applies any unapplied atrial pacing therapies in the third sequence until the episode of atrial tachycardia is terminated, the cycle length of the atrial rhythm is regular, or all of the atrial pacing therapies in the third sequence have been applied.

34. The system of claim 33, wherein the controller:
disarms each of the applied atrial pacing therapies in the third sequence to prevent reapplication of the applied atrial pacing therapies in the third sequence during the episode of atrial tachycardia; and
following a predetermined period of time, rearms the applied atrial pacing therapies in the third sequence to permit reapplication of the applied atrial pacing therapies in the third sequence during the episode of atrial tachycardia.

35. The system of claim 34, wherein the atrial pacing therapies in the third sequence are arranged in sequential order from least aggressive to most aggressive.

36. The system of claim 35, wherein the atrial pacing therapies in the third sequence include an atrial burst therapy, atrial ramp therapy, and atrial cardioversion.

37. The system of claim 20, wherein the controller:
applies a shock therapy to the heart in the event the irregular heart rhythm satisfies criteria for application of the shock therapy; and
just prior to applying the shock therapy, reapplies a sequence of the atrial pacing therapies to attempt to terminate the episode of atrial tachycardia.

38. The system of claim 20, wherein the detector and the controller are contained in an implantable housing, the system further comprising an implantable lead that delivers the applied atrial pacing therapy to the heart.

39. A method comprising:
detecting an episode of atrial tachycardia in a heart;
detecting a condition of the atrial tachycardia;
selecting one of several sequences of the atrial pacing therapies based on the detected condition;
applying the atrial pacing therapies in the selected sequence to treat the atrial tachycardia;
disarming each of the applied atrial pacing in the selected sequence to prevent reapplication of the applied atrial pacing therapies for the detected condition during the episode of atrial tachycardia; and
following a predetermined period of time, rearming the applied atrial pacing therapies in the selected sequence to permit reapplication of the applied atrial pacing therapies for the detected condition during the episode of atrial tachycardia.

40. The method of claim 39, wherein the detected condition is a cycle length of the atrial rhythm.

41. The method of claim 39, wherein the detected condition is a combination of a cycle length and regularity of the atrial rhythm.

42. The method of claim 39, wherein at least some of the atrial pacing therapies in the sequences are substantially identical.

43. The method of claim 39, further comprising applying each of the atrial pacing therapies in the selected sequence until the episode of atrial tachycardia is terminated, the detected condition of the atrial rhythm changes, or all of the atrial pacing therapies in the selected sequence have been applied.

44. A system comprising:

a detector that detects an episode of atrial tachycardia in a heart and a condition of the atrial tachycardia; and a controller that selects one of several sequences of the atrial pacing therapies based on the detected condition, applies the atrial pacing therapies in the selected sequence to treat the atrial tachycardia, disarms each of the applied atrial pacing in the selected sequence to prevent reapplication of the applied atrial pacing therapies for the detected condition during the episode of atrial tachycardia, and following a predetermined period of time, rearms the applied atrial pacing therapies in the selected sequence to permit reapplication of the applied atrial pacing therapies for the detected condition during the episode of atrial tachycardia.

45. The system of claim 44, wherein the detected condition is a cycle length of the atrial rhythm.

46. The system of claim 44, wherein the detected condition is a combination of a cycle length and regularity of the atrial rhythm.

47. The system of claim 44, wherein at least some of the atrial pacing therapies in the sequences are substantially identical.

48. The system of claim 44, wherein the controller apples each of the atrial pacing therapies in the selected sequence until the episode of atrial tachycardia is terminated, the detected condition of the atrial rhythm changes, or all of the atrial pacing therapies in the selected sequence have been applied.

49. A computer-readable medium carrying instructions to cause a processor to:

detect an episode of atrial tachycardia in a heart;

detect a condition of the atrial tachycardia;

select one of several sequences of the atrial pacing therapies based on the detected condition;

apply the atrial pacing therapies in the selected sequence to treat the atrial tachycardia;

disarm each of the applied atrial pacing in the selected sequence to prevent reapplication of the applied atrial pacing therapies for the detected condition during the episode of atrial tachycardia; and following a predetermined period of time, rearm the applied atrial pacing therapies in the selected sequence to permit reapplication of the applied atrial pacing therapies for the detected condition during the episode of atrial tachycardia.

\* \* \* \* \*